US006534672B2

(12) United States Patent
Salem et al.

(10) Patent No.: US 6,534,672 B2
(45) Date of Patent: Mar. 18, 2003

(54) FLUID BED VINYL ACETATE CATALYST

(75) Inventors: George Frederick Salem, Shaker Heights, OH (US); Michael James Baker, Feltham (GB)

(73) Assignee: The Standard Oil Company, Chicago, IL (US)

( * ) Notice: Subject to any disclaimer, the term of this patent is extended or adjusted under 35 U.S.C. 154(b) by 0 days.

(21) Appl. No.: 10/004,780

(22) Filed: Dec. 4, 2001

(65) Prior Publication Data

US 2002/0062039 A1 May 23, 2002

Related U.S. Application Data

(60) Division of application No. 09/455,753, filed on Nov. 15, 1999, now Pat. No. 6,358,882, which is a continuation-in-part of application No. 09/207,851, filed on Dec. 8, 1998, now abandoned.

(51) Int. Cl.[7] .......................... C07C 67/00; C07C 27/10; C07C 67/05
(52) U.S. Cl. .................. 560/241; 560/241.1; 560/244; 560/245
(58) Field of Search .............................. 560/241, 241.1, 560/244, 245; 502/242, 262, 303–305, 326, 339, 349, 350

(56) References Cited

U.S. PATENT DOCUMENTS

| 4,321,409 A | | 3/1982 | Yoshida et al. ............. 560/244 |
| 5,466,652 A | | 11/1995 | Papaizos et al. ............. 502/330 |
| 5,536,693 A | * | 7/1996 | Lemanski et al. ........... 502/300 |
| 5,550,281 A | | 8/1996 | Cirjak et al. ................ 560/245 |
| 5,571,771 A | * | 11/1996 | Abel et al. .................. 502/330 |
| 5,591,688 A | | 1/1997 | Blum et al. ................. 502/330 |
| 5,622,908 A | * | 4/1997 | Abel et al. .................. 502/339 |
| 5,665,667 A | * | 9/1997 | Lemanski et al. .......... 502/300 |
| 5,691,267 A | * | 11/1997 | Nicolau et al. ............. 502/330 |
| 5,710,318 A | | 1/1998 | Cirjak et al. ................ 560/245 |
| 5,808,136 A | * | 9/1998 | Tacke et al. ................ 560/243 |
| 5,859,287 A | | 1/1999 | Nicolau et al. ............. 560/241 |

FOREIGN PATENT DOCUMENTS

| CA | 2313644 | 6/2000 |
| CA | 2314247 | 6/2000 |
| EP | 0723810 | 7/1996 |
| EP | 0839793 | 5/1998 |
| GB | 1283737 | 8/1972 |
| GB | 1333449 | 10/1973 |
| GB | 1500167 | 2/1978 |
| JP | 6279841 | 4/1987 |
| JP | 1148342 | 6/1989 |
| ZA | 9811287 | 6/1999 |

* cited by examiner

Primary Examiner—Mark L. Bell
Assistant Examiner—Patricia L. Hailey
(74) Attorney, Agent, or Firm—Wallace L. Oliver

(57) ABSTRACT

A catalytically active material useful to prepare vinyl acetate monomer from ethylene, acetic acid, and an oxygen-containing gas under fluid bed conditions comprises a porous microspheroidal support containing catalytically active palladium crystallites finely dispersed within the support. This catalyst material does not require incorporation of gold to maintain activity and selectivity. A process to produce a vinyl acetate fluid bed catalyst in which catalytically active small palladium crystallites are finely dispersed within the support comprises dispersing selected metal species within the support which have an affinity to palladium to form very fine crystallites of palladium. The affinity metal species may be dispersed by impregnation onto a preformed microspheroidal support or may be intimately incorporated within the support before impregnation with a soluble palladium species.

42 Claims, No Drawings

FLUID BED VINYL ACETATE CATALYST

CROSS-REFERENCE TO RELATED APPLICATIONS

This application is a division of U.S. application Ser. No. 09/455,753, filed Nov. 15, 1999, now U.S. Pat. No. 6,358,882 B1, which is a continuation-in-part of U.S. application Ser. No. 09/207,851, filed Dec. 8, 1998, abandoned, all incorporated by reference herein.

BACKGROUND OF THE INVENTION

This invention relates to a catalyst and catalyst support useful in producing vinyl acetate monomer (VAM) in a fluid bed process and more particularly relates to an active and selective fluid-bed VAM catalyst suitable for use in a fluid bed reactor in which catalytically active metal is well dispersed within a support.

Conventionally, vinyl acetate monomer is produced in the gas phase by reacting ethylene, acetic acid, and oxygen in the presence of a supported catalyst in a fixed bed reactor. In this type of reactor, a support material such as silica or alumina is impregnated with a catalytic metal such as palladium in combination with gold and an alkali metal salt, typically in the form of an acetate. A requirement of a fixed bed reactor process is that the supported catalyst formed into relatively large structural shapes such as balls and may be 2 to 50 mm in diameter or more.

In early examples of fixed-bed catalysts, palladium and gold are distributed more or less uniformly throughout the carrier, e.g., U.S. Pat. Nos. 3,275,680, 3,743,607 and 3,950,400 and Great Britain Patent No. 1,333,449 and South African Patent No. 687,990. Since gaseous reactants do not diffuse significantly into the large fixed-bed catalyst structure, much of the expensive catalytic metal components in the interior of the catalyst were not useful. Subsequently, fixed-bed catalysts were developed in which most of the catalyst metals were deposited onto the outer shell of the supported catalyst. For example, Great Britain Patent No. 1,500,167 describes a catalyst structure in which at least ninety percent of the palladium and gold is distributed in that part of the carrier particle which is not more than thirty percent of the particle radius from the surface. In addition, Great Britain Patent No. 1,283,737 teaches that the degree of penetration into the porous carrier can be controlled by pretreating the porous carrier with an alkaline solution of, for example, sodium carbonate or sodium hydroxide. Another approach to produce an active catalyst is described in U.S. Pat. No. 4,048,096 and other methods of producing shell-impregnated catalyst are disclosed in U.S. Pat. Nos. 4,087,622 and 5,185,308. Shell impregnated catalysts containing elements in addition to palladium and gold such as lanthanide compounds include U.S. Pat. No. 5,859,287 and WO 99/29418. In other fixed bed catalysts described in EP-A-0723810, a silica support may be impregnated with a Group IA, IIA, IIIA, or IVB metal salt and then calcined before addition of palladium and gold. Each of these patents primarily is concerned with the manufacture of fixed bed catalyst useful for the manufacture of vinyl acetate.

A new approach to produce vinyl acetate monomer is to use a fluid-bed process in which gaseous reactants are contacted continuously with small supported catalyst particles under fluidized bed conditions. Expected benefits of a fluidized bed VAM process include a simpler fluid bed reactor design than a multi-tubular fixed bed reactor and increased catalyst life due to decreased hot spots which are typical of a fixed bed reactor. Further, continuous addition of make-up catalyst maintains catalyst performance and eliminates complete catalyst change-out and shut-downs. Higher production rates may be achieved because higher oxygen levels safely may be fed into a fluid-bed reactor without producing a flammable mixture. Recently-issued U.S. Pat. Nos. 5,591,688, 5,665,667, and 5,710,318, assigned to the assignee of the present invention and incorporated by reference herein, are directed to the production of fluid bed vinyl acetate catalyst, or a fluid bed process for the manufacture of vinyl acetate.

In any regard, conventional commercially acceptable VAM catalyst, whether used in fixed or fluid-bed reactor systems, uses gold in combination with the palladium metal species, such as described in U.S. Pat. No. 5,859,287 and European Published Application EP 0 723 810, incorporated by reference herein. It is believed that gold forms an alloy with the palladium and inhibits agglomeration or sintering of palladium particles during the life of the catalyst under process conditions. Although other metals have been suggested as substitutes for gold in catalyst systems, gold has been found to be required for commercially practicable catalyst in terms of activity and selectivity. However, gold is an expensive component in the catalyst preparation. Therefore, there is a need for a commercially useful catalyst that does not require, or minimizes, the presence of gold.

Further, there is a continuing need for VAM catalysts, especially fluid bed catalysts, which have more advantageous activity/selectivity characteristics and which are more resistant to attrition. As described in this specification, the catalyst and catalyst support of this invention show commercially significant activity/selectivity properties without a necessity of gold as a catalyst component. Further, catalyst particles of this invention typically show improved attriton resistance under normal fluid bed conditions.

SUMMARY OF THE INVENTION

A catalytically active material useful to produce vinyl acetate monomer from ethylene, acetic acid, and an oxygen-containing gas under fluid bed conditions comprises a porous microspheroidal support containing catalytically active palladium crystallites finely dispersed within the support. The catalyst material does not require incorporation of gold to maintain activity and selectivity.

A process to produce a vinyl acetate fluid bed catalyst in which catalytically active small palladium crystallites are finely dispersed within the support comprises dispersing selected metal species within the support which have an affinity to palladium to form very fine crystallites of palladium. The affinity metal species may be dispersed by impregnation onto a preformed microspheroidal support or may be intimately incorporated within the support before impregnation with a soluble palladium species.

DESCRIPTION OF THE PREFERRED EMBODIMENT(S)

The vinyl acetate catalysts of this invention, suitable for use in a fluid bed reactor system, contain catalytically active palladium crystallites finely dispersed within microspheroidal supports. It is believed that small, finely dispersed crystallites maintain catalytic activity and selectivity without a necessity of incorporation of gold in the catalytic material.

In one aspect of this invention, catalytically-active palladium crystallites are incorporated within a support particle, suitable for use in a fluid bed reactor system, such that the palladium crystallites are well dispersed in an interior region of the particle. In preferable catalysts, palladium crystallites are contained in an interior region of the catalyst particle and not concentrated at the surface. Although there may be a gradation of palladium crystallite concentration from below the surface to the particle center, the palladium crystallites appear finely dispersed in TEM photomicrographs, i.e., the palladium crystallites are substantially evenly distributed within the region without prominent agglomerations. In comparison to similarly produced particles using palladium and gold, which show significant numbers of agglomerated Pd/Au crystallites, a preferable catalyst particle of this invention shows few, if any, agglomerated palladium crystallites.

Typically, palladium crystallites in catalyst particles of this invention are no more than about 20 nanometers (nm) in mean diameter. In preferred catalysts of this invention, reduced metal crystallites in the catalyst particle including palladium crystallites are less than about 15 nm and more preferably less than about 10 nm. Typical crystallites are between about 5 to about 15 nm.

In order to form the fine palladium crystallites within a microspheroidal support according to this invention, a metal species that binds or has an affinity to palladium must be well dispersed with in the support particle. These affinity metal species include lanthanides such as lanthanum and cerium and Group 3 and Group 4 (IUPAC Periodic Series system) metals such as titanium and zirconium. Unlike use is of gold that forms a gold/palladium alloy, these affinity metals, when well dispersed into the support particles, do not form agglomerations of palladium crystallites. Thus, without agglomeration there should be a greater palladium crystallite surface area available for catalytic sites.

According to this invention, one method to prepare the catalytically active supported materials comprises contacting solutions of palladium and the added affinity metal species with a preformed particulate support. All of the metal species should be completely dissolved in a suitable solvent medium, preferably water, at sufficiently low temperature that agglomerations of metal do not accumulate on the support particle during preparation. Preferably, impregnation with a soluble metal species is conducted at ambient temperature. Thus, the solvent medium and the metal species are chosen to achieve complete solubility, preferably at ambient temperatures, such as 10 to 40° C. and usually 20 to 30° C. As described below, the impregnated support is reduced to form metal crystallites within the support particle that are believed to be the catalytically active sites. Preferably, the reduction step follows the impregnation, although there may be intermediate drying of the catalyst particles to facilitate handling of the materials. There is no need to "fix" the soluble metal salts onto the support with alkaline species as is necessary to form "shell" fixed bed catalysts before reduction.

In another method to prepare catalytically active supported materials, the affinity metal is intimately distributed throughout the support material, in contrast to a mere physical mixture of two materials or an affinity metal species impregnated into the pores of the support and then calcined. For example, in the preparation of a porous silica support useful in this invention, an oxide of an affinity metal such as cerium oxide, titanium oxide, or zirconium oxide may be incorporated in the silica sol during support preparation. In a preferred method, an oxide of the affinity metal replaces a portion of silica particles incorporated into the silica sol prior to spray drying which forms the preformed support particles used in this invention. In another preferred embodiment, a sol of an affinity metal oxide may be used in preparation of a preformed catalyst support. Mixtures of affinity metal oxides may be incorporated into the preformed supports used in this invention. In the preformed catalyst supports of this invention containing an intimate distribution of an affinity metal oxide, the affinity metal oxide is part of the porous support structure as an oxide.

In a further embodiment, solutions of affinity metal species may be impregnated onto preformed support particles containing affinity metal oxides in intimate association with the support structure.

The catalyst useful in this invention is supported on a microspheroidal particulate material suitable for use in a fluid bed process. As is well known in the fluid bed art, these particles must be small enough to be maintained in a fluid bed state under reaction conditions while keeping sufficient attrition resistance such that excessive amounts of catalyst need not be replenished during the process. Further, although typical particle sizes (as measured by mean particle diameters) should not be so large as to be difficult to keep in a fluid bed state, there should not be an excess amount of very small particles (fines) which are difficult to remove from the system and may plug gas recycle lines. Thus, typically suitable fluid bed catalyst particles have a distribution of larger to smaller particle sizes within the particle size limits.

In the process of this invention, typically, at least 50% of the particles are less than about 105 microns, preferably at least 75% of the particles are less than 105 microns and more preferably at least 85% are less than 105 microns. In a typical catalyst useful in this invention, there may be less than 1 to 5% of particles more than 105 microns. Further, typically, less than 50% are less than 44 microns and preferably less than 35% are less than 44 microns. A typical catalyst may contain about 25 to 30% of the particles less than 44 microns. A typical catalyst useful in this invention has at least 50% of the particles with mean diameters between 44 and 88 microns. Persons skilled in the art will recognize that particles sizes of 44, 88, and 105 microns are arbitrary measures in that they are based on standard sieve sizes. Particle sizes and particle size distributions may be measured by an automated laser device such as a Microtrac 100.

Microspheroidal particles useful in this invention are sufficiently porous to permit gaseous reactants to diffuse into the particle and contact catalytic sites incorporated within the particle. Thus, the pore volume should be high enough to permit gaseous diffusion. However, a particle with an exceedingly high pore volume typically will not have sufficient attrition resistance or will not have sufficient surface area for catalytic activity. A typically sufficient microspheroidal particle has a pore volume (measured by mercury porosimetry) between about 0.2 and 0.7 cc/gram. A preferable particle has a pore volume between about 0.3 and 0.65 cc/g and more preferably between about 0.4 and 0.55 cc/g.

Surface areas (measured by BET) for particles with mean diameters and pore volumes useful in this invention typically are above about 50 $m^2/g$ and may range up to about 200 $m^2/g$. A typical measured surface area is about 60 to about 125 $m^2/g$.

Although silica-based supports are the most preferred in this invention, other oxides may be used as long as a particle of appropriate size and with sufficient pore volume is produced on which may be placed the required catalytic materials. Possible oxides include alumina, silica-alumina, titania, zirconia and mixtures thereof.

Typically useful supports, especially silica supports are described in U.S. Pat. No. 5,591,688, incorporated by reference herein. In these supports a microspheroidal particle is produced by spray drying a mixture of a silica sol with silica particles followed by drying and calcining. In the preparation, at least 10 wt. %, preferably at least 50 wt. %, of a silica sol is mixed with particulate silica. A useful particulate silica is a fumed silica such as Aerosil® (De Gussa Chemical Company). A typical silica particulate material has a high surface area (about 200 $m^2/g$) with essentially no micropores, and, typically, are aggregates (with mean diameters of several hundred nm) of individual particles with average diameters of about 10 nm (above 7 nm). Preferably, the silica is sodium free. Sufficient particulate silica is added to the mixture to obtain a desired pore volume in the resulting support particle. The amount of particulate silica may range up to 90 wt. % and typically ranges up to 10 to 50 wt. % of the silica in the mixture. Typically, the silica sol/particulate silica mixture is spray dried at an elevated temperature such as between 115° to 280° C., preferably 130° to 240° C., followed by calcining at temperature typically ranging from between 550° to 700° and, preferably 630° to 660° C.

As part of this invention, a portion or all of the particulate silica may be replaced by an affinity metal species such as an oxide of cerium, titanium, zirconium, or lanthanum. Typically, 0.5 to 20 wt. % or more, preferably 1 to 5 wt. % of the particulate silica is substituted with these oxides.

Alternatively, a sol may be produced from an oxide other than silica or in combination with silica. In this embodiment, a particulate oxide is added to a sol, such as a sol of ceria, titania, zirconia, as described above for silica materials, and the resulting mixture spray dried to produce a preformed catalyst support particle. The particulate material may be silica, an oxide of an affinity metal, or a combination thereof. Other compatible metal oxides may be present so long as there also is a sufficient distribution of affinity metal in the particle to form the catalyst of the invention. The resulting particle should be microspheroidal and porous as described and should contain the affinity metal oxide well distributed throughout the catalyst particle, such that incorporation of palladium and subsequent reduction will form a distribution of palladium crystallites according to this invention.

Although catalysts of this invention typically may not require the presence of gold for activity and selectivity, gold may be added as an optional component, especially to maintain long-term stability or integrity. Gold may be a useful component in a catalyst particle in which an affinity metal (e.g., Ce) is incorporated into the preformed support during preparation. However, the amount of gold typically will be less than used in conventional catalysts and could be present in amounts up to 5 wt. %, preferably up to 3 wt. %, and many times less than 1 wt. %, in the catalyst material.

An advantageous silica sol useful in this invention contains silica particles in the sol typically more than 20 nanometers in mean diameter and may be up to about 100 nanometers or more. Preferable sols contain silica particles of about 40 to 80 nanometers. Nalco silica sol 1060 particularly is advantageous because of the relatively large mean silica particle sizes of 60 nm pack less efficiently than smaller sol particles such as Nalco 2327 at about 20 nm. The larger particle size sol yields a final support with higher mesopore volume and less micropore volume.

A suitable catalyst also contains an alkali metal (most preferably potassium) salt as a promoter up to about 10 wt. %, preferably up to 5 to 8 wt. %, and more preferably up to about 4 wt. % (calculated as alkali metal). Typically, at least 0.1 wt. % of alkali metal is present in the catalyst and more preferably at least 1 wt. %. A typical catalyst composition contains 0.5 to 2 wt. % palladium and 1 to 3 wt. % potassium. The preferred salt is acetate. Usually, the alkali metal salt is added as a solution, using the incipient wetness technique to control the amount of alkali metal salt placed on the catalyst particle, after impregnation of the palladium species and subsequent reduction. In an alternate embodiment, the alkali metal may be added to the first impregnation solution.

A catalyst useful in this invention typically contains at least about 0.1 wt. %, preferably at least 0.2 wt. % palladium to about 5 wt. % and preferably up to 4 wt. % palladium. As indicated above, palladium is incorporated into the support material preferably by incipient wetness to control the amount of palladium on the support.

The amount of affinity metal used typically is commensurate (although not necessarily equivalent) with the amount of palladium to be incorporated into the catalyst. A catalyst may contain at least about 0.1 wt. %, preferably at least 0.2 wt. % affinity metal to about 10 wt. % or more and preferably up to 5 wt. % of the metal.

In preparation of a catalyst of this invention, advantageously, the impregnated metal species incorporated within the support, such as palladium and cerium species, are reduced by contact with a suitable reducing agent. This reduction will transform the impregnated palladium species to catalytically active zero valence palladium (Pd(0)) crystallites. Typical reducing agents known to the art include hydrogen, hydrides, alkanes, alkenes, hydrazine, and the like. Preferably, hydrazine (most preferably in an aqueous solution) is used to reduce the metal species. Reduction with aqueous hydrazine after impregnation is preferable. Typically, an excess of reducing agent is used to complete the reaction.

Preferably, impregnated and reduced catalyst particles are washed with a suitable solvents such as water to remove excess reducing agent as well as undesired anions such as halides. Washing may be performed several times with portions of wash liquid until the desired level of contaminants is reached. Typically, the washed particles are dried slowly before addition of a promoter such as potassium acetate.

A preferable method to prepare the catalyst of this invention comprises contacting solutions of palladium and of at least one affinity metal with a preformed porous microspheroidal support. The metal species should be completely dissolved in the solvent medium at sufficiently low temperatures such that agglomeration of metal species does not accumulate in the support particle during preparation. Preferably, the impregnation with soluble metal species is conducted at ambient temperature. Thus, the solvent medium and the metal species are chosen to achieve complete solubility, preferably, at ambient temperature. Typical useful metal salts contain halide and the typical solvent is deionized or distilled water. Typical soluble salts useful in this invention include salts of tetrachloropalladic acid, such as sodium or potassium tetrachloropalladate, palladium chloride or palladium chloride dihydrate, palladium selenate, palladium sulfate, tetrammininepalladium (III) chloride, and the like. Tetrachloropalladate is preferred. Similarly, other soluble metal salts of affinity metals, such as chlorides, bromides, iodides, nitrates may be used. Halide salts, preferably chloride salts, typically are used. Since acetate salts of palladium and affinity metals are sparingly soluble in water or acetic acid, these salts typically would not be used in this invention.

These soluble metal salts may be impregnated onto the support particle through known procedures. A preferable method to impregnate salt solutions is an incipient wetness technique in which an amount of salt solution measured to fill the pores of the support without excess solution is used. Thus, a desired level of palladium and other metal species may be placed onto the support by calculating the amount of metals and the volume of solution needed to fill the pores. Since, typically, the solution impregnated support is allowed to dry slowly without washing, all of the metals in the impregnation solution will be incorporated into the support.

In a typical procedure, the preformed microspheroidal support is impregnated with a solution (or solutions) of the metal salts (palladium and at least one affinity metal) using an incipient wetness technique. Compounds of the active metal, palladium, and affinity metal component are dissolved in the appropriate ratios in a suitable solvent. The support material then is added to a solution containing the catalytically active metal (Pd) and affinity metal species and stirred to allow the active metal and promoter element to impregnate the microspheroidal support material. The impregnated catalyst support is dried slowly at an elevated temperature, such as 40 to 80° C., typically overnight. Preferably, the impregnated metal species are reduced to form active palladium crystallites, washed to remove halide and reducing agent, and dried. The dried material is added to a second solution containing a promoter alkali metal salt, preferably potassium acetate. This second solution is heated to evaporate the solvent to obtain a dried catalyst as described above. The final, dry catalyst may be used for the production of vinyl acetate from feed preferably containing ethylene, acetic acid, and an oxygen-containing gas in a fluid bed reactor system.

It is preferable that the impregnated metal species salts (Pd and affinity metals) are dissolved in a single portion of solvent. The amount of solvent is such that the pore volume of the support is completely filled with the first solution. However, in some instances a desired affinity metal may not be soluble in the same solvent as the other metal compounds to be used. In this case, a solution containing some of the metal components may be impregnated upon the support, followed by impregnating a second solution containing the remaining components. Solvents that are useful include water and volatile organic solvents such as carboxylic acids with four carbons or fewer, alcohols, ethers, esters, and aromatics. The preferred solvent is water. In a further embodiment of the present invention, the affinity metals may be placed onto the finished catalyst by incorporating the affinity metals during the manufacture of the microspheroidal support.

The catalysts of the present invention may be used in a fluid bed reactor for the reaction of ethylene and acetic acid with oxygen to produce vinyl acetate under fluid bed reaction conditions. The reaction temperature suitably is maintained at about 100° to 250° C., preferably 130° to 190° C. The reaction pressure suitably is about 50 to 200 psig (3 to 14 bars), preferably 75 to 150 psig (5 to 10 bars). In a fluid bed reactor system, the catalyst particles are maintained in a fluidized state by sufficient gas flow through the system. This gas flow preferably is maintained at a level close to the minimum rate required to maintain the fluidization. Excess flow rate may cause channeling of the gas through the reactor which decreases conversion efficiency. Additional alkali metal salt promoter may be added during process to maintain activity.

The following Examples illustrate but do not limit the invention described and claimed herein.

EXAMPLES 1–9

Comparative Run A

A series of Example and Comparative Run experiments was conducted to test catalyst materials of this invention. In these experiments, a completely dissolved aqueous solution of sodium tetrachlorpalladate in combination with a completely dissolved aqueous solution of a selected affinity metal was impregnated onto a preformed microspheroidal support (either a Support 1 or Support 2 material described below) by an incipient wetness technique. In this technique a measured amount of impregnating solution was contacted at ambient temperature with the support in an amount determined only to fill the pores of the support without excess liquid. The resulting impregnated solid was dried at 60° C. overnight. The dried solid which incorporated the metal species was reduced by contact with an aqueous hydrazine solution (prepared as 3 grams of hydrazine hydrate per 80 ml of water) to reduce the metal species and the resulting solution was filtered and washed multiple times with deionized water to remove hydrazine and residual chloride as confirmed by a silver nitrate test. The resulting solid was dried at 60° C. overnight and further impregnated by incipient wetness with an aqueous solution of potassium acetate in an amount to provide the desired amount of potassium in the catalyst and dried at 60° C. overnight. About two grams of the resulting catalyst material was combined with an inert diluent (Ce/K or Au/K on Support 1 which had been shown to be inert under the reaction conditions used) to produce about 30 cc of total solid. This total solid was charged to the microreactor as described below. Results are shown in Table 1.

Support Preparation

Two types of preformed microspheroidal supports were prepared and used in the examples of present invention: (1) support material comprising 100% silica and (2) support material comprising silica in combination with other known inert support materials such as alumina, ceria, titania and zirconia. Prior to use, the supports were sieved and a specific particle size distribution of the support was used in the catalyst preparations:

5% of the particles are less than 105 microns but greater than 88 microns

70% of the particles are less than 88 microns but greater than 44 microns

25% of the particles are less than 44 microns

Support 1

Support 1 was prepared by spray drying a mixture of Nalco (Nalco Chemical Company) silica sol 1060 and DeGussa Aerosil® (DeGussa Chemical Company) 200 silica according to U.S. Pat. No. 5,591,688. In the dried support, 80% of the silica came from the sol and 20% of the silica came from the Aerosil®. The spray dried microspheres were calcined in air at 640° C. for 4 hours.

Support 2

A series of supports was prepared by spray drying a mixture of Nalco (Nalco Chemical Company) silica sol 1060, Degussa (Degussa Chemical Company) Aerosil® 200 silica, and an additional oxide such as cerium oxide, titanium dioxide, zirconium oxide, aluminum oxide, or silica/aluminum oxide mixtures (such as Aerosil® MOX 170 or Aerosil® COK 84). In the dried support, 80% of the silica came from the sol, 20% of the silica came from the Aerosil®, and 1 to 3% by weight of the Aerosil® was replaced by oxides cerium or titanium. The spray dried microspheroidal support containing cerium was calcined in air at 640° C. for 4 hours.

Reactor Testing

The prepared catalysts were tested in a bench scale fluid bed reactor with a maximum catalyst capacity of 40 cubic centimeters. Sufficient catalyst was used such that the oxygen conversion was limited to 30% in order to directly compare catalyst activity. A total catalyst loading of 30 cubic centimeters volume was obtained by mixing sufficient inert microspheroidal material described above with an active catalyst prior to reactor testing. The reactor was equipped with two feed inlets with ethylene, acetic acid, oxygen, and some nitrogen entering the reactor through the lower inlet and nitrogen only fed through a central inlet.

Reactor pressure was controlled via a back-pressure regulator reactor temperature was maintained at 152C.° and all lines leading to and from the reactor were heat traced and maintained at 160±5 C.°.

The gaseous reactor effluent was analyzed on-line using a Hewlett Packard Model 5890 gas chromatograph equipped with both thermoconducitivity (TCD) and flame ionization (FID) detectors. Oxygen, nitrogen, ethylene and carbon dioxide were separated on a 13X molecular sieve column parallel with 23% SP1700 on 80/100 Chromosorb PAW, and quantified with the TCD. Vinyl acetate and acetic acid were separated on a 4% DP-1701 capillary column and quantified with the FID.

Activity (grams of vinyl acetate product per kilogram of catalyst per hour) and selectivity (moles of vinyl acetate product per mole of ethylene feed) were calculated from these data.

TABLE 1

| Example (Run) | Support Type - Diluent | Au (wt. %) | Pd (wt. %) | K (wt. %) | Impregnated affinity metal (wt. %) | Affinity metal in support (wt. %) | Activity g. of VAM/ Kg. of cat./ hr. | Selectivity VAM to ethylene (%) |
|---|---|---|---|---|---|---|---|---|
| A | I-Au/K | 0.65 | 1.60 | 2.80 | — | — | 1617 | 94.6 |
| 1 | I-Ce/K | — | 1.60 | 2.74 | Ce (0.60) | — | 2174 | 94.8 |
| 2[1] | I-Ce/K | — | 0.81 | 2.65 | Ce (1.16) | — | 2774 | 91.8 |
| 3 | I-Au/K | — | 1.61 | 2.80 | La (0.65) | — | 1772 | 93.9 |
| 4 | II-Ce/K | 0.56 | 1.38 | 2.51 | — | Ce (0.2) | 1857 | 94.6 |
| 5 | II-Ce/K | — | 1.41 | 2.52 | — | Ce (0.2) | 1846 | 98.9 |
| 6 | II-Ce/K | — | 1.50 | 2.66 | Ce (0.57) | Ce (0.6) | 1752 | 92.1 |
| 7 | II-Au/K | 0.54 | 1.42 | 2.67 | — | Ti (0.4) | 1858 | 91.9 |
| 8 | II-Au/K | — | 1.44 | 2.66 | — | Ti (0.6) | 2158 | 94.2 |
| 9 | II-Ce/K | — | 1.41 | 2.70 | Ce (0.65) | Ti (0.6) | 2007 | 94.7 |

[1]Metals reduced with a diluted stream of hydrogen (1% in nitrogen) at 180° C.

The data illustrate that catalysts of this invention maintain activity and selectivity without the necessary presence of gold. Further, catalysts of this invention incorporating cerium showed an increased attrition resistance during fluid bed testing.

These examples and accompanying specification have illustrated the invention in terms of specific embodiments. Those skilled in the art recognize modifications and variations to be within the intended scope of the following claims.

We claim:

1. A method to produce vinyl acetate comprising contacting ethylene, acetic acid, and an oxygen-containing gas in a fluid bed reactor under fluid bed reaction conditions with a catalyst formed by:

contacting a preformed porous microspheroidal support with solutions of a palladium compound and at least one affinity metal compound such that the palladium and affinity metal are finely dispersed into the microspheroidal support;

reducing the palladium compound to Pd(0) crystallites;

adding a promoter comprising an alkali metal salt to the support; and recovering the resulting catalyst material.

2. The method of claim 1 wherein the affinity metal comprises a Group 3 or 4 metal or a lanthanide.

3. The method of claim 1 wherein the affinity metal is cerium or lanthanum.

4. The method of claim 1 wherein the affinity metal is titanium or zirconium.

5. The method of claim 1 wherein the promoter alkali metal salt is potassium acetate.

6. The method of claim 1 wherein the preformed microspheroidal support is contacted with solutions of halide-containing salts of palladium and affinity metal.

7. The method of claim 1 wherein the preformed porous microspheroidal support is contacted with a solution of a palladium compound and a solution of at least one affinity metal compound in separate steps.

8. The method of claim 1 wherein an affinity metal oxide is intimately incorporated within the preformed microspheroidal support prior to impregnation with a palladium compound.

9. The method of claim 1 in which the preformed microspheroidal support comprises silica.

10. The method of claim 1 wherein the solutions of a palladium compound and affinity metal compound are aqueous solutions.

11. The method of claim 1 in which the catalyst material does not contain gold.

12. The method of claim 1 wherein the palladium crystallites are less than about 10 nanometers in mean diameters.

13. A method to produce vinyl acetate comprising contacting ethylene, acetic acid, and an oxygen-containing gas in a fluid bed reactor under fluid bed reaction conditions with a catalyst formed by:

preforming porous microspheroidal support particles in which an affinity metal species is intimately dispersed within the microspheroidal support particles;

contacting the preformed porous microspheroidal support with a solution of a palladium compound such that the palladium metal is finely dispersed into the microspheroidal support;

reducing the palladium compound to Pd(0) crystallites;

adding a promoter comprising an alkali metal salt; and recovering the resulting catalyst material.

14. The method of claim 13 wherein the affinity metal incorporated into the preformed support comprises a Group 3 or 4 metal or a lanthanide.

15. The method of claim 14 wherein the promoter alkali metal salt is potassium acetate.

16. The method of claim 14 wherein the affinity metal is cerium, lanthanum, titanium, or zirconium.

17. The method of claim 16 in which solutions of at least one affinity metal compound are impregnated onto the microspheroidal support.

18. The method of claim 17 in which a solution of a cerium compound is impregnated onto the microspheroidal support.

19. The method of claim 13 wherein the solution of a palladium compound is an aqueous solution.

20. The method of claim 13 in which porous microspheroidal support particles are preformed by adding an oxide of an affinity metal with silica particles to a silica sol and spray drying to form porous microspheroidal particles.

21. The method of claim 20 wherein affinity metal oxide is an oxide of cerium or titanium or a mixture thereof.

22. The method of claim 13 in which porous microspheroidal support particles are preformed by adding silica particles to a sol of an oxide of an affinity metal and spray drying to form porous microspheroidal particles.

23. The method of claim 22 in which silica particles with an affinity metal oxide are added to the sol.

24. The method of claim 13 in which the catalyst material does not contain gold.

25. A method to produce vinyl acetate comprising contacting ethylene, acetic acid, and an oxygen-containing gas in a fluid bed reactor under fluid bed reaction conditions with a catalyst comprising catalytically active palladium crystallites incorporated in a microspheroidal support structure with an alkali metal salt promoter in which the palladium crystallites are finely dispersed throughout the microspheroidal structure.

26. The method of claim 25 in which the catalyst material does not contain gold.

27. The method of claim 26 wherein the porous preformed microspheroidal support is a silica with a pore volume between about 0.3 to about 0.65 cc/gram which contains cerium as an affinity component.

28. A method of claim 27 in which contains about 1 to 5 wt. % potassium.

29. The method of claim 28 in which at least a portion of the cerium is incorporated into the preformed microspheroidal support.

30. The method of claim 29 wherein a portion of the cerium is impregnated onto the preformed microspheroidal support.

31. The method of claim 30 wherein the porous preformed microspheroidal support has a distribution of particle sizes such that at least 50% of the particles have mean diameters less than 105 microns, at least 50% of the particles have mean diameters between 44 and 88 microns, and no more than 5% of the particles have a mean diameter over 105 microns and the palladium crystallites are less than 10 nm in mean diameter and comprise 0.2 to 4 wt. % of the catalyst.

32. The method of claim 31 wherein at least a portion of the cerium is incorporated into the preformed microspheroidal support and a portion of the cerium is impregnated onto the preformed microspheroidal support.

33. The method of claim 25 wherein the mean diameters of palladium crystallites are less than about 10 nanometers.

34. The method of claim 25 in which the catalyst material contains an effective amount of at least one affinity component comprising a Group 3 or 4 metal or a lanthanide.

35. The method of claim 34 in which the affinity component is lanthanum or cerium.

36. The method of claim 34 in which the affinity component is titanium or zirconium.

37. The method of claim 34 in which the affinity component is impregnated onto the support.

38. The method of claim 34 in which the affinity component is incorporated into the support during support preparation.

39. The method of claim 25 wherein the microspheroidal support is a silica or silica/alumina.

40. The method of claim 25 wherein the microspheroidal support is a porous silica having a distribution of particle sizes such that at least 50% of the particles have mean diameters less than 105 microns and at least 50% of the particles have mean diameters between 44 and 88 microns.

41. The method of claim 25 wherein the microspheroidal support has a pore volume between about 0.2 and 0.7 cc/gram.

42. The method of claim 25 wherein the microspheroidal support has a surface area above about 50 $m^2$/gram.

* * * * *